United States Patent [19]

Perrin et al.

[11] Patent Number: 4,460,799

[45] Date of Patent: Jul. 17, 1984

[54] PROCESS FOR THE PREPARATION OF ORTHO-HYDROXYBENZYL ALCOHOLS

[75] Inventors: Robert Perrin, St. Didier au Mont d'Or; Roger Fugier, Rantigny, both of France

[73] Assignee: Isover Saint-Gobain, Courbevoie, France

[21] Appl. No.: 391,467

[22] Filed: Jun. 23, 1982

[30] Foreign Application Priority Data

Jun. 25, 1981 [FR] France ................................ 81 12470

[51] Int. Cl.³ ........................ C07C 37/20; C07C 39/12
[52] U.S. Cl. .................................... 568/764; 568/716; 568/724; 568/753; 568/727
[58] Field of Search ............... 568/716, 727, 764, 846, 568/724, 753

[56] References Cited

U.S. PATENT DOCUMENTS

| | | | |
|---|---|---|---|
| 3,290,393 | 12/1966 | Marchand et al. | 568/764 |
| 4,192,959 | 3/1980 | Bauer et al. | 568/764 |
| 4,238,629 | 12/1980 | Bauer et al. | 568/764 |

FOREIGN PATENT DOCUMENTS 1328945  4/1963  France ................................ 568/764

*Primary Examiner*—Werren B. Lone
*Attorney, Agent, or Firm*—Pennie & Edmonds

[57] ABSTRACT

This invention relates to a process for the selective preparation of ortho-hydroxybenzyl alcohols and, in particular, ortho-hydroxybenzyl alcohol. According to the invention, the reaction of a phenol with an aldehyde in an initially anhydrous medium and in the presence of a catalytic amount of a metal phenate, results in the selective production of ortho-hydroxybenzyl alcohols.

8 Claims, No Drawings

PROCESS FOR THE PREPARATION OF ORTHO-HYDROXYBENZYL ALCOHOLS

TECHNICAL FIELD

This invention relates to a process for the selective preparation of ortho-hydroxybenzyl alcohols and, in particular, ortho-hydroxybenzyl alcohol, by the reaction of a phenol with an aldehyde in the presence of a catalytic amount of a metal phenate.

BACKGROUND ART

Ortho-hydroxybenzyl alcohols have a wide range of uses for various technical applications. Ortho-hydroxybenzyl alcohol, commonly known as saligenol or saligenin, is particularly useful for its intrinsic pharmacological properties as well as for its intermediate role in the synthesis of insecticides and, for example, products used in the manufacture of perfumes.

Various methods for the production of ortho-hydroxybenzyl alcohols, including saligenol, have been proposed. Saligenol may be prepared from natural products through the reaction of salicin and emulsin. The major drawback of this process is the low yield of the desired saligenol reaction product, which is on the order of 15%.

French Pat. No. 1,328,945 discloses the reaction of formaldehyde with an aryl metaborate to provide saligenol in yields on the order of 65%, expressed in relation to the phenol and formaldehyde reactants. This process is characterized by several disadvantages. Any formaldehyde which is not transformed into saligenol is lost either because it becomes part of a reaction by-product or is otherwise non-recoverable. Although the boric acid is not transformed in the reaction process, it is effectively non-recoverable due to the high cost of recovery techniques.

According to European Pat. No. 0,007,285, saligenol is prepared by the reaction of phenol boric esters—obtained by the reaction of at least 1.1 mole of a phenol with 1 mole of boric acid—with formaldehyde. This process provides improved saligenol yields in terms of the phenol and formaldehyde used in the reaction. The primary disadvantage of this reaction scheme is that it requires the use of solvents such as benzene, toluene and xylene in the preparation of the phenol boric ester reactant as well as, optionally, in the formaldehyde/phenol boric ester condensation reaction. The use of such solvents is accompanied by pollution and recycling problems.

Another proposed method for producing hydroxybenzyl alcohols involves the condensation of formaldehyde with a phenol in the presence of a basic alkali or alkaline-earth hydroxide catalyst such as, for example, sodium, potassium, lithium, or calcium hydroxide. The resulting end product, however, is a mixture of saligenol and para-hydroxybenzyl alcohol, from which the separation of saligenol is both difficult and costly.

SUMMARY OF THE INVENTION

This invention effectively eliminates the various disadvantages inherent in known processes for producing ortho-hydroxybenzyl alcohols. The applicants have discovered that, unexpectedly, ortho-hydroxybenzyl alcohols and, in particular, saligenol, can be selectively prepared via a condensation reaction of a phenol with an aldehyde, in an initially anhydrous reaction medium, in the presence of a catalytic amount of a metal phenate. Advantageously, the reaction medium does not require the presence of any organic or aqueous solvent, thus allowing a reaction characterized by its low cost, energy-efficiency and lack of inherent toxic residue or recycling problems.

DETAILED DESCRIPTION OF THE INVENTION

According to the invention, ortho-hydroxybenzyl alcohols, and in particular, saligenol, are selectively prepared by the reaction of a phenol with an aldehyde, particularly formaldehyde, in a condensed medium that is initially anhydrous and in the presence of a catalytic amount of a metal phenate.

Examples of metal phenates useful in the process include aluminum phenates, such as aluminum phenate, aluminum hydroxydiphenate, and aluminum triphenate, as well as gallium phenate. Preferably, the metal phenate catalyst is an aluminum phenate, which has a base of a nonpolluting, inexpensive metal. Aluminum triphenate is particularly advantageous because it is easily prepared just before its use in the reaction system. Use of a metal phenate catalyst, such as aluminum phenate, in the reaction according to the invention leads to a yield of the desired saligenol end product that is on the order of about 90% or higher in relation to the amount of transformed phenol.

Under an advantageous embodiment of the invention, an aluminum phenate catalyst is used to produce saligenol from the reaction of phenols and aldehydes, particularly, phenol and formaldehyde, at a concentration of at least about 0.1 mole of catalyst per 100 moles of phenol and at a reaction temperature between about 50° and 150° C., preferably between about 80° and 100° C.

The use of aluminum phenate as a catalyst for the ortho-alkylation of phenol has been proposed. For example, when phenol is reacted with α-methylstyrene in the presence of an aluminum phenate catalyst, the principal component of the resulting ortho-cumyl phenol/para-cumyl phenol reaction mixture is the ortho product, *Angew. Chemie*, Vol. 69, 124 (1957); *Zh, Org. Khim.* Vol. 10, 2, 359–64 (1974). Alkylation or dialkylation reactions of phenol in the ortho position are also described in *Angew. Chemie*, Vol. 69, 699, 746 (1957) and French Pat. No. 1,422,944. Even in view of these disclosures, the selective production of ortho-hydroxybenzyl alcohols via an aluminum phenate-catalyzed reaction is totally unexpected. Aluminum phenate, itself, exhibits an acidic character and, as is well known to those skilled in the art, the presence of acidic catalysts in conventional condensation reactions of phenols with aldehydes leads to the formation of polymers such as novolak resins.

The metal phenate catalyst is advantageously prepared just before its use in the reaction between the phenol and the formaldehyde. This preparation sequence eliminates the possibility of partial hydrolysis of the catalyst and diminution of catalytic activity. Preferably, the catalyst is prepared in the reaction medium itself. Any excess phenol present in the reaction medium is thus advantageously and completely utilized during either the preliminary catalyst formation reaction or the subsequent reaction between the phenol and formaldehyde. Thus, a reaction step to separate the catalyst from the medium in which it is formed is unnecessary.

The formaldehyde used in the production of saligenol can be in the form of gaseous formaldehyde or paraformaldehyde. The overall condensation reaction is more rapid when gaseous formaldehyde is used. The use of a gaseous formaldehyde reactant advantageously results in a modification of the reaction operating conditions and has no appreciable influence on the overall ortho-hydroxybenzyl product yield.

According to an advantageous embodiment of the invention, the formaldehyde reactant is anhydrous formaldehyde. The use of this anhydrous aldehyde reactant, which is not likely to supply water during the course of the reaction, is advantageous because, for example, any water potentially supplied by the depolymerization of paraformaldehyde can lead to a partial decomposition of the moisture-sensitive aluminum phenate catalyst.

Advantageously, the molar ratio of formaldehyde to phenol in the reaction according to the invention is the stoichiometric ratio. With this type of ratio of reactants, the problem of separation of the reaction products is greatly minimized, if not totally avoided. When the formaldehyde to phenol ratio is greater than 1:1 and, particularly when it is on the order of 2:1 or more, the reaction time is much longer than when the reactants are present in a stoichiometric ratio; this is also true when paraformaldehyde is used. In addition, it has been observed that when the formaldehyde to phenol molar ratio is much greater than the stoichiometric ratio, the overall reaction yield is less than that resulting from a reaction carried out with stoichiometric amounts of reagents. Slight excesses or deficiencies of one of the reactants does not, however, lead to appreciable modifications in either the reaction yield or the operating conditions.

EXAMPLES

The following examples illustrate various aspects and advantages of the process of this invention. The examples are set forth for the purpose of illustration only and are not to be construed as limiting the scope of the invention in any manner.

Example 1

One mole or 94 g of phenol at a temperature of 85° C. is introduced into a 250 ml glass reactor which is equipped with an agitator, a thermometer, a jacket in which 85° C. water circulates, a sampling cock and a $CaCl_2$ guard. One mole, or 30 g of formaldehyde, in the form of paraformaldehyde, is added.

After a period of about 30 minutes, during which the paraformaldehyde is partially depolymerized, 0.0123 mole or 3.77 g of anhydrous aluminum phenate powder is added. The anhydrous aluminum phenate powder has previously been prepared by, for example, the direct addition of aluminum turnings to boiling phenol or by the reaction of aluminum isopropylate on phenol.

The condensation reaction is permitted to continue for about 2 hours 50 minutes. Progress of the reaction is monitored by gas or liquid phase chromatography.

The resulting reaction mixture has the following composition:
49.8 g phenol
53.3 g saligenol
0 g para-hydroxybenzyl alcohol The saligenol yield is 91.5% in relation to the phenol consumed.

Separation of the reaction products can be effected by known aqueous phase/organic phase extraction processes such as types described in German Pat. Nos. 2,729,075 and 2,915,216.

Alternatively, saligenol can be separated from the remaining phenol by the method described in French Pat. No. 1,338,945 and European Pat. No. 0,007,285, in which the saligenol is complexed into a borate complex form, from which the saligenol is subsequently liberated by saponification, alcoholysis or hydrolysis.

Example 2

Aluminum phenate is prepared by the addition of a mixture of 30 g of phenol and 0.83 g of aluminum turnings into a 250 ml glass reactor, which is equipped with an agitator and an intake for a neutral gas such as, for example, dry nitrogen. The mixture is heated by a heating flask at 180° C. for 30 minutes. After cooling, a crystallized mixture of 0.0307 mole of aluminum phenate and 0.277 mole of phenol is obtained.

In the reactor equipment described in Example 1, 0.773 mole of phenol is brought to a temperature of 85° C. One mole of formaldehyde, in the form of paraformaldehyde, is added. After about 30 minutes, the previously prepared aluminum phenate-phenol mixture is added, bringing the reaction medium content of phenol to 1 mole.

The reaction is continued as in Example 1 and the resulting reaction mixture has the following composition:
64.0 g phenol
36.0 g saligenol
0 g para-hydroxybenzyl alcohol The saligenol yield is 90.6% in relation to the phenol consumed.

Example 3

One mole of phenol at a temperature of 85° C. is introduced into the equipment described in Example 1. One mole of formaldehyde, in the form of paraformaldehyde, is added. After a period of about 30 minutes, during which the paraformaldehyde is partially depolymerized, 0.02 mole of aluminum hydroxydiphenate is added.

The reaction is continued as in Example 1 and the resulting reaction mixture has the following composition:
66.0 g phenol
35.0 g saligenol
0 g para-hydroxybenzyl alcohol As demonstrated by this example, aluminum hydroxydiphenate exhibits catalytic activity similar to that of aluminum triphenate in the selective preparation of saligenol.

Example 4

One mole of phenol at a temperature of 85° C., is introduced into the equipment of Example 1. Two moles of formaldehyde, in the form of paraformaldehyde, are added. After about 30 minutes, 0.012 mole of anhydrous aluminum triphenate is added. The condensation reaction is allowed to continue for about 2 hours 30 minutes.

The resulting reaction mixture, analyzed by chromatography, is found to have the following composition:
66.4 g phenol
40.0 g saligenol
0 g para-hydroxybenzyl alcohol The fact that the saligenol yield is less than that in Example 1 is attributable to the presence of a certain amount of water, resulting from the depolymerization of paraformaldehyde, which is, most likely, responsible for partial decomposition of the aluminum triphenate catalyst.

Example 5

The reaction conditions are identical to those in Example 1, except that the temperature of the reaction mixture is maintained at 75° C. during the condensation reaction.

After a reaction time of 2 hours 50 minutes, chromatographic analysis of the reaction shows that the amount of saligenol obtained is less than that obtained in Example 1.

Example 6

One mole of phenol at a temperature of 85° C. is introduced into a 500 ml reactor which is equipped with an agitator, a thermometer, a jacket in which 85° C. water circulates, a sampling cock and a $CaCl_2$ guard. Approximately 0.012 mole of aluminum triphenate, in powder form, is added to the reactor. Gaseous formaldehyde, prepared simultaneously by the heating of paraformaldehyde suspended in silicone oil, is added to the reaction medium.

After 1 mole of gaseous formaldehyde has been introduced, the reaction mixture is analyzed by liquid phase chromatography and is found to have the following composition:
49.0 g phenol
54.0 g saligenol
0 g para-hydroxybenzyl alcohol The saligenol yield is approximately 91% in relation to the phenol consumed.

We claim:

1. A process for the selective preparation of ortho-hydroxy benzyl alcohol, which comprises reacting a phenol with formaldehyde in an initially anhydrous reaction medium in the presence of an aluminum or gallium phenate, with a catalyst:phenol molar ratio of at least 0.1:100, at about 50° to 150° C. to form a reaction mixture containing unreacted phenol and ortho-hydroxy benzyl alcohol, and separating the ortho-hydroxy benzyl alcohol from the remaining phenol.

2. The process according to claim 1 wherein the aldehyde is formaldehyde or paraformaldehyde.

3. The process according to claim 2 wherein the formaldehyde is in gaseous form.

4. The process according to claim 1 wherein the aluminum phenate is aluminum phenate, aluminum hydroxydiphenate or aluminum triphenate.

5. The process according to claim 1 wherein the catalyst is prepared in the reaction medium.

6. The process according to claim 1 wherein the phenol and formaldehyde are used in a stoichiometric ratio.

7. The process according to claim 1 wherein the ortho-hydroxybenzyl alcohol produced is salignol.

8. The process according to claim 1 wherein the reaction products are separated from the remaining phenol by an aqueous phase-organic phase extraction process.

* * * * *